(12) United States Patent
Skelton et al.

(10) Patent No.: US 8,700,174 B2
(45) Date of Patent: Apr. 15, 2014

(54) RECHARGE COUPLING EFFICIENCY FOR PATIENT POSTURE STATE

(75) Inventors: Dennis M. Skelton, Bloomington, MN (US); Jon P. Davis, St. Michael, MN (US); Rajeev M. Sahasrabudhe, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 476 days.

(21) Appl. No.: 13/016,444

(22) Filed: Jan. 28, 2011

(65) Prior Publication Data

US 2012/0197322 A1    Aug. 2, 2012

(51) Int. Cl.
*A61N 1/08* (2006.01)

(52) U.S. Cl.
USPC .................................. 607/61; 320/108; 607/2

(58) Field of Classification Search
USPC ....................................................... 607/60, 61
See application file for complete search history.

(56) References Cited

U.S. PATENT DOCUMENTS

| | | | |
|---|---|---|---|
| 7,076,304 B2 | 7/2006 | Thompson | |
| 7,167,756 B1 | 1/2007 | Torgerson et al. | |
| 7,177,690 B2 | 2/2007 | Woods et al. | |
| 7,248,929 B2 | 7/2007 | Meadows et al. | |
| 7,505,816 B2 | 3/2009 | Schmeling et al. | |
| 7,515,967 B2 | 4/2009 | Phillips et al. | |
| 7,650,192 B2 | 1/2010 | Wahlstrand | |
| 2006/0247737 A1 | 11/2006 | Olson et al. | |
| 2008/0300654 A1 | 12/2008 | Lambert et al. | |
| 2010/0013383 A1 | 1/2010 | Skelton et al. | |
| 2010/0256710 A1* | 10/2010 | Dinsmoor et al. | 607/61 |
| 2010/0280440 A1 | 11/2010 | Skelton et al. | |

OTHER PUBLICATIONS

International Search Report and Written Opinion dated Jan. 25, 2012 for corresponding PCT Application No. PCT/US2011/054165, (10 pgs.).

* cited by examiner

*Primary Examiner* — Kennedy Schaetzle
*Assistant Examiner* — Erica Lee
(74) *Attorney, Agent, or Firm* — Shumaker & Sieffert, P.A.

(57) ABSTRACT

In general, the disclosure relates to implantable medical devices including rechargeable power sources. In one example, the disclosure relates to a device including a rechargeable power source, a recharge module configured to recharge the rechargeable power source via inductive energy transfer, a posture state sensor configured to generate posture sensor data; and a processor. The processor may be configured to determine recharge coupling efficiency during a recharge session, receive posture sensor data generated by the posture sensor during the recharge session, and associate the recharge coupling efficiency determined during the recharge session with the posture sensor data.

24 Claims, 10 Drawing Sheets

US 8,700,174 B2

RECHARGE COUPLING EFFICIENCY FOR PATIENT POSTURE STATE

TECHNICAL FIELD

The disclosure relates to implantable medical devices (IMDs), and, more particularly, IMDs including rechargeable power sources.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient can be provided with a patient programming device. The patient programming device communicates with a medical device to allow the patient to activate therapy and/or adjust therapy parameters. For example, an IMD, such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure relates to IMDs employing one or more rechargeable power sources to supply power for the IMD, for example, to delivery therapy to a patient. When implanted in a patient, the rechargeable power source of an IMD may be recharged periodically by an external charging device via transcutaneous inductive coupling. During a recharge session, the recharge coupling efficiency of the charging process may be monitored, e.g., by a processor of the IMD. The processor of the IMD also may monitor patient posture sensor data generated by a posture sensor. In some examples, the posture sensor data generated during the recharge session may be indicative of the posture state occupied by a patient during the recharge session. The recharge coupling efficiency and the posture sensor data during the recharge session may be associated with each other on a temporal basis. In some examples, the recharge coupling efficiency exhibited while a patient occupied one or more posture states during a recharge session may be determined based on the association on a posture state specific basis.

In one example, the disclosure relates to a method comprising determining recharge coupling efficiency for an implantable medical device during a recharge session, receiving posture sensor data generated by a posture sensor during the recharge session, and associating the recharge coupling efficiency determined during the recharge session with the posture sensor data.

In another example, the disclosure relates to a system comprising a rechargeable power source, a recharge module configured to recharge the rechargeable power source via inductive energy transfer, a posture sensor configured to generate posture sensor data, and a processor configured to determine recharge coupling efficiency during a recharge session, receive posture sensor data generated by the posture sensor during the recharge session, and associate the recharge coupling efficiency determined during the recharge session with the posture sensor data.

In another example, the disclosure relates to a system comprising means for determining recharge coupling efficiency for an implantable medical device during a recharge session, means for receiving posture sensor data generated by a posture sensor during the recharge session, and means for associating the recharge coupling efficiency determined during the recharge session with the posture sensor data.

In another example, the disclosure relates to a non-transitory computer-readable storage medium comprising instructions to cause one or more processors to determine recharge coupling efficiency for an implantable medical device during a recharge session, receive posture sensor data generated by a posture sensor during the recharge session, and associate the recharge coupling efficiency determined during the recharge session with the posture sensor data.

In another example, the disclosure relates to a non-transitory computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more examples of the invention are set forth in the accompanying drawings and the description below. Other features, objects, and advantages of the invention will be apparent from the description and drawings, and from the claims.

DETAILED DESCRIPTION

Figure 1:
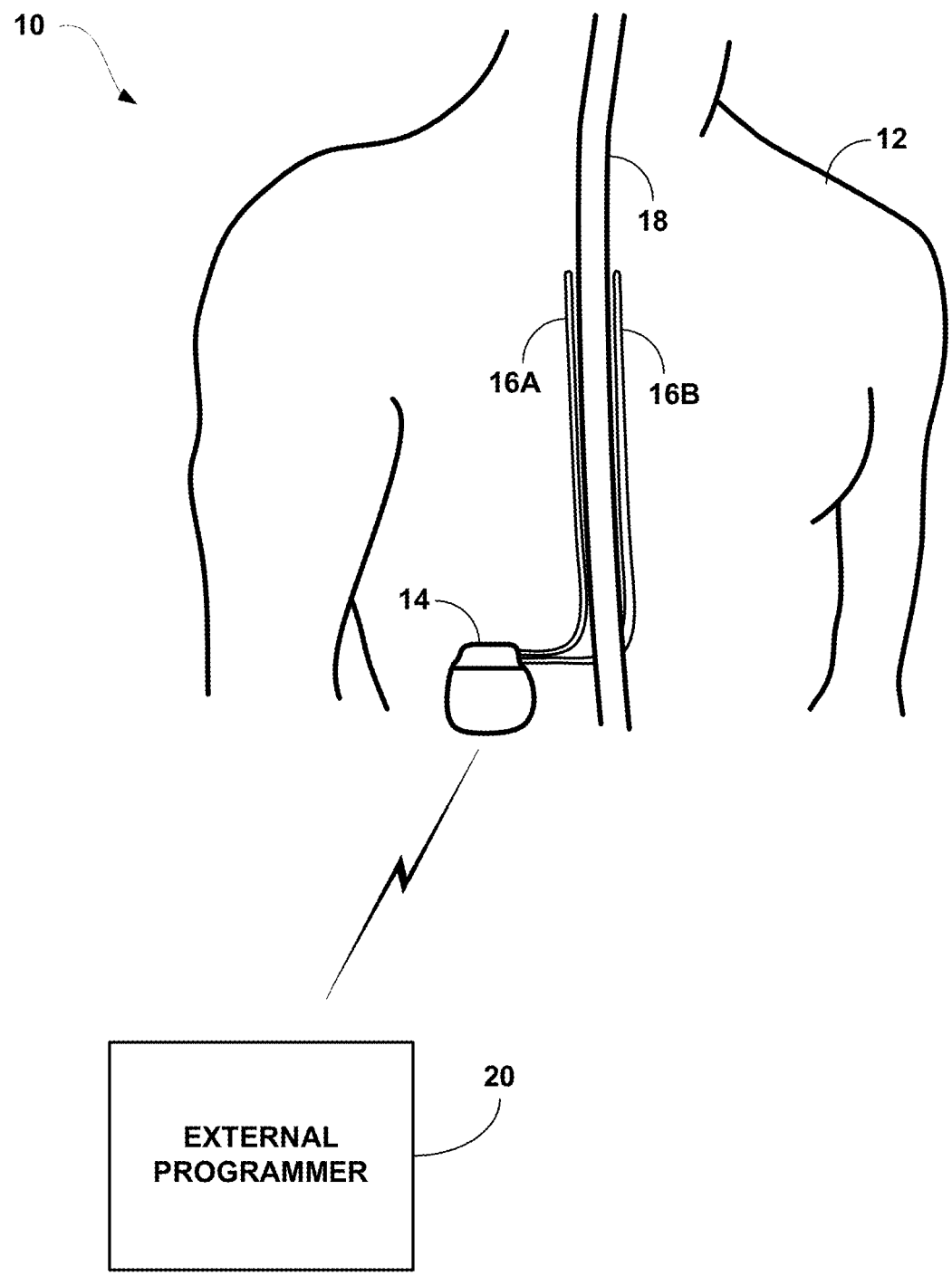
FIG. 1 is a conceptual diagram illustrating an example implantable stimulation system including two implantable stimulation leads.

In some examples, an IMD including a rechargeable power source may be configured to deliver therapy to a patient. Examples of therapies delivered to a patient include electrical stimulation therapy and/or non-electrical stimulation therapy, such as therapeutic fluid delivery therapy. For purposes of illustration, the examples in this disclosure will be described with respect to the delivery of electrical stimulation therapy. However, it is understood that, in some examples, the same or similar principles may be applicable to the delivery of non-electrical stimulation therapy.

The foregoing types of IMDs require electrical power to perform their therapeutic function, which may include driving an electrical infusion pump, providing an electrical neurostimulation pulse, providing a muscle stimulation pulse, or providing an electrical cardiac stimulation pulse or shock. This electrical power is derived from a power source.

In some examples, the power source may include a rechargeable power source, such as, e.g., a rechargeable battery or capacitor. When at least a portion of the capacity of the rechargeable power source has been expended, e.g., due to the operation of IMD, the power source may be recharged via electrical energy trancutaneously transferred through inductive coupling. Transcutaneous energy transfer through the use of inductive coupling involves the placement of two coils positioned in close proximity to each other on opposite sides of the skin (i.e., cutaneous boundary). One of these coils is external to the patient, and is placed against the patient's skin in the vicinity of the IMD. This external coil (which may be referred to as a "primary coil") may be associated with a power source of an external charger device. A secondary coil is implanted within the patient, and may be contained within the housing of the IMD or otherwise associated therewith.

In one example, when positioned in close proximity to each other, the primary coil may be driven by the external power source with an alternating current. This induces a current in the secondary coil by way of inductive coupling. The induced current in the secondary coil may be used to charge or recharge one or more batteries associated with the implanted power source of the IMD. Such an operation may take place during a recharge session, at which time a patient may temporarily position the primary coil of a charging device proximate the secondary coil of the IMD to recharge all or a portion of the power source capacity. In some examples, during a recharge session, the patient may have one or more external components associated with the charging device attached to his or her body. Such attachment may impair the patient's mobility and limit the patient's comfort. The higher the efficiency of the energy transfer system, the faster the desired recharging can be completed, thus limiting inconvenience to the patient.

Recharge coupling efficiency (or "coupling efficiency") refers to the strength of the coupling between the secondary coil of the IMD and the primary coil of the recharging unit. During a recharge session, the stronger the coupling between the secondary coil and primary coil, the greater the amount of energy that may be transferred from the charger device to the secondary coil per unit time. In some examples, recharge coupling efficiency may be expressed in terms of percentages, e.g., with 100 percent coupling efficiency reflecting the maximum or optimal coupling between the secondary and primary coil in terms of energy transfer and 0 percent coupling efficiency reflecting a state in which substantially no energy is transferred from the charging device to the secondary coil. The recharge coupling efficiency between the charging device and IMD may be influenced by the position of the primary and secondary coils relative to each other. In this sense, the recharge coupling efficiency may reflect the position of the primary antenna of the charger unit relative to the secondary coil.

During a recharge process, a patient may attempt to position the primary coil of a charger in a position relative to the secondary coil of an IMD that provides for a relatively high level of recharge coupling efficiency. However, the position of the primary coil and secondary relative to each other may be influenced by the posture state of a patient. As such, the recharge coupling efficiency may vary during a recharge session due to changes in the position of the secondary coil relative to the primary coil associated with transitions in patient posture state or other movement during the recharge session. In some examples, higher recharge coupling efficiency may be attained during a recharge session while a patient occupies certain posture states compared to that of other posture states.

In accordance with some examples of the disclosure, an IMD and/or other device may monitor the recharge coupling efficiency during a recharge session to recharge a power source of the IMD. Additionally, the IMD and/or other device may receive posture sensor data generated by one or more posture sensors during the recharge session. The posture sensor data may be indicative of one or more posture states occupied by the patient during the recharge session. The IMD and/or other device may then associate the posture sensor data with the recharge coupling efficiency determined during the recharge session, e.g., on a temporal basis. In some instances, such information may allow a user to evaluate the information from one or more prior recharge sessions to determine if there is any relationship between the recharge coupling efficiency.

In some examples, an IMD and/or other device may detect the one or more posture states occupied by the patient during the recharge session based on the received posture state data. The IMD and/or other device may then associate the one or more posture states with the recharge coupling efficiency during the recharge session by determining, for example, the average recharge coupling efficiency detected while occupying respective posture states. Additionally, the IMD and/or other device may determine the time the patient spent occupying respective posture states during the recharge session. Such a process may be employed to evaluate one or more multiple recharge sessions.

Such information may be displayed to a user via an external display device, such as, e.g., an external programming device, to allow a user to detect if one or more relationships exist between the recharge coupling efficiency and patient posture state during recharge sessions. In some instances, a patient may tailor his or her posture state behavior during future recharge sessions if such information indicates a history of desired or undesired recharge coupling efficiencies when the patient occupies one or more particular posture states relative to other posture states. In particular, a patient may select a particular posture state to occupy during a recharge session if that posture state is associated with a desired level of recharge coupling efficiency. By selecting a posture state that provides desirable recharge coupling efficiency, the patient may be able to reduce the required recharge time. Alternatively, such information may illustrate that the recharge coupling efficiency is substantially the same for all posture states of the patient, in which case the patient may choose to freely occupy each of those posture states during future recharge sessions without having to worry about his or her posture state negatively influencing the recharge coupling efficiency of the recharge operation.

In some examples, an IMD and/or other device may monitor the received posture sensor data to detect one or more changes to the posture sensor data greater than some threshold amount during a recharge session. In some examples, the threshold amount may be defined to correspond to movement of the patient and/or IMD beyond some nominal amount. For example, the threshold amount may be defined to detect changes in the posture sensor data corresponding to posture changes of the patient, and/or bumps or other mechanical forces applied to the IMD. The IMD and/or other device may associate the recharge coupling efficiency detected at or near the time of the change in the posture sensor data. In some examples, such information may be used as a diagnostic tool when troubleshooting issues with the process used to recharge the power source of an IMD.

The posture sensor data may include values for one or more measurable parameters of the output signal generated by a posture sensor, especially those parameters used to determine the posture state of a patient. In some examples, a posture sensor used by an IMD to detect patient posture set may include an accelerometer sensor. For ease of description, examples of the disclosure are described primarily with regard to a 3-axis accelerometer as the posture sensor that generates an output signal for each axis, i.e., an output signal for each of the x, y, and z axis. However, examples of the disclosure are not limited as such. In some examples, an IMD may detect patient posture state via multiple single-axis accelerometers, dual-axis accelerometers, 3-axis accelerometers, or some combination thereof, or may include a sensor other than an accelerometer. In the case of a 3-axis accelerometer, posture sensor data may include a signal value sampled from the output signal for each axis generated by the accelerometer. In some examples, the signal value for one or more of the axes may be an average value determined based on a plurality of sampled signal values. Additionally or alternatively, posture sensor data may include a magnitude and/or angle of a posture vector derived from the values of each axis of the accelerometer sensor within a 3-dimensional vector space. Example techniques for determining the posture state of a patient based on such posture sensor data are described further below.

FIG. 1 is a schematic diagram illustrating an implantable stimulation system 10 including a pair of implantable electrode arrays in the form of stimulation leads 16A and 16B. Although the techniques described in this disclosure are generally applicable to a variety of implantable medical devices (IMDs), application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As will be described below, IMD 14 may be configured to detect the posture state of patient 12, and delivery therapy to patient 12 according to the detected posture state. The postures state of patient 12 may be detected by IMD 14 based on the output of one or more posture sensors (e.g., one or more accelerometers) associated with IMD 14. However, examples are contemplated in which IMD 14 does not deliver therapy according to the detected posture state of patient 12. Furthermore, in some examples, IMD 14 may be implanted for reasons other than delivering therapy to patient 12. For example, techniques described in this disclosure may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

As shown in FIG. 1, system 10 includes an IMD 14 and external programmer 20 shown in conjunction with a patient 12, who is ordinarily a human patient. In the example of FIG. 1, IMD 14 is an implantable electrical stimulator that delivers SCS, e.g., for relief of chronic pain or other symptoms. Stimulation energy is delivered from IMD 14 to spinal cord 18 of patient 12 via one or more electrodes of implantable leads 16A and 16B (collectively "leads 16"). In some applications, such as SCS to treat chronic pain, the adjacent implantable leads 16 may have longitudinal axes that are substantially parallel to one another.

Although FIG. 1 is directed to SCS therapy, system 10 may alternatively be directed to any other condition that may benefit from stimulation therapy. For example, system 10 may be used to treat tremor, Parkinson's disease, epilepsy, urinary or fecal incontinence, pelvic pain, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), pelvic floor stimulation, gastric stimulation, or any other stimulation therapy. In these cases, the leads may be implanted in different locations other than the spinal cord.

Each of leads 16 may include electrodes (not shown in FIG. 1), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms, such as continuous waveforms. Programs that control delivery of other therapies by IMD 14 may include other parameters, e.g., such as dosage amount, rate, or the like for drug delivery.

In the example of FIG. 1, leads 16 carry one or more electrodes that are placed adjacent to the target tissue of the spinal cord. One or more electrodes may be disposed at a distal tip of a lead 16 and/or at other positions at intermediate points along the lead. Electrodes of leads 16 transfer electrical stimulation generated by IMD 14 to tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration. Leads 16 may be implanted within patient 12 and directly or indirectly (e.g., via a lead extension) coupled to IMD 14. In additional examples, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 in via any suitable region, such as the thoracic, cervical or lumbar regions. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

In the example of FIG. 1, stimulation energy is delivered by IMD 14 to the spinal cord 18 to reduce the amount of pain perceived by patient 12. As described above, IMD 14 may be used with a variety of different therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 generates and delivers stimulation therapy according to one or more programs. A program defines values for one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

During use of IMD 14 to treat patient 12, movement of patient 12 among different posture states may affect the ability of IMD 14 to deliver consistent efficacious therapy. For example, posture state changes may present changes in symptoms or symptom levels, e.g., pain level. As another example, a patient posture state may affect the relative location between the electrodes of leads 16 and a target therapy site. For example, leads 16 may migrate toward IMD 14 when patient 12 bends at the waist, resulting in displacement of electrodes relative to the target stimulation site and possible disruption in delivery of effective therapy. Stimulation energy transferred to target tissue may be reduced due to electrode migration, which may reduce therapeutic efficacy in terms of relief of symptoms, e.g., pain or an increase in undesirable side effects.

As another example of how posture state may affect the relative location between the electrodes of leads 16 and a target therapy site, leads 16 may be compressed towards spinal cord 18 when patient 12 lies down. Such compression may cause an increase in the amount of stimulation energy transferred to the target tissue. An increase in stimulation energy transferred to the target stimulation site may cause unusual sensations or an otherwise undesirable intensity of therapy, which may both be considered undesirable side effects that undermine overall efficacy. Thus, in some examples, the amplitude of stimulation therapy may need to be decreased when patient 12 is lying down to avoid causing patient 12 additional pain or unusual sensations resulting from the increased compression near electrodes of leads 16. The additional pain or unusual sensations may be considered undesirable side effects that undermine overall efficacy.

Many other examples of reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 includes a posture state module that detects the posture state of patient 12 and causes the IMD 14 to automatically adjust stimulation according to the detected posture state. For example, a posture state module may include one or more posture sensors such as an accelerometer sensor that detects when patient 12 lies down, stands up, or otherwise changes posture.

In response to a posture state indication by the posture state module, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

A posture state may refer to a patient posture or a combination of posture and activity. For example, some posture states, such as upright, may be sub-categorized as upright and active or upright and inactive. Other posture states, such as lying down posture states, may or may not have an activity component, but regardless may have sub-categories such as lying face up or face down, or lying on the right side or on the left side. As will be described below, various posture states may be defined, at least in part, by different sets of posture state reference data. In some examples, posture sensor data received from a posture sensor when patient 12 occupies a particular posture state may be used to define, at least in part, posture state reference data corresponding to the respective posture state. The posture state reference data for a posture state may define, for example, a reference coordinate vector and a region around the reference coordinate vector. For example, the region around the reference coordinate vector may include a range of coordinates within a predetermined distance from the reference coordinate vector. In operation, a posture sensor module associated with IMD 14 compares posture sensor data to the posture state reference data to detect the posture occupied by the patient.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

Referring still to FIG. 1, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy modifications relating to changes in the posture state of patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

As will be described below, in addition to that of programming IMD 14, external programmer 20 may also be configured to charge one or more rechargeable power sources of IMD 14. In particular, external programmer 20 may include a primary coil which may be inductively coupled to a secondary coil associated with IMD 14 to transcutaneously transfer electrical energy used to charge a power source of IMD 14 that has become partially or fully depleted, e.g., due to the delivery of electrical stimulation to patient 12 via IMD 14 over a period of time. While a combined programmer/charger unit is described in the disclosure, in other examples, an external charger device primarily used to recharge a power source of IMD 14 may be embodied separate from an external programmer device configured primarily for the programming of IMD 14.

In accordance with some examples of this disclosure, the recharge coupling efficiency may be determined, e.g., by one or more processors of IMD 14 and/or programmer 20, during a recharging session. Additionally, during the recharge session, IMD 14 and/or programmer 20 may receive posture sensor data generated by one or more posture sensors. The posture sensor data received during the recharge session may be indicative of the one or more posture states occupied by the patient during the recharge session. IMD 14 and/or programmer 20 may associate the recharge coupling efficiency determined during the recharge session with the posture sensor data received during the recharge session. Such an association may be made by IMD 14 and/or programmer 20 on a temporal basis. Again, this information may be evaluated to determine the relationship, if any, between patient posture state and recharge coupling efficiency.

Figure 2:
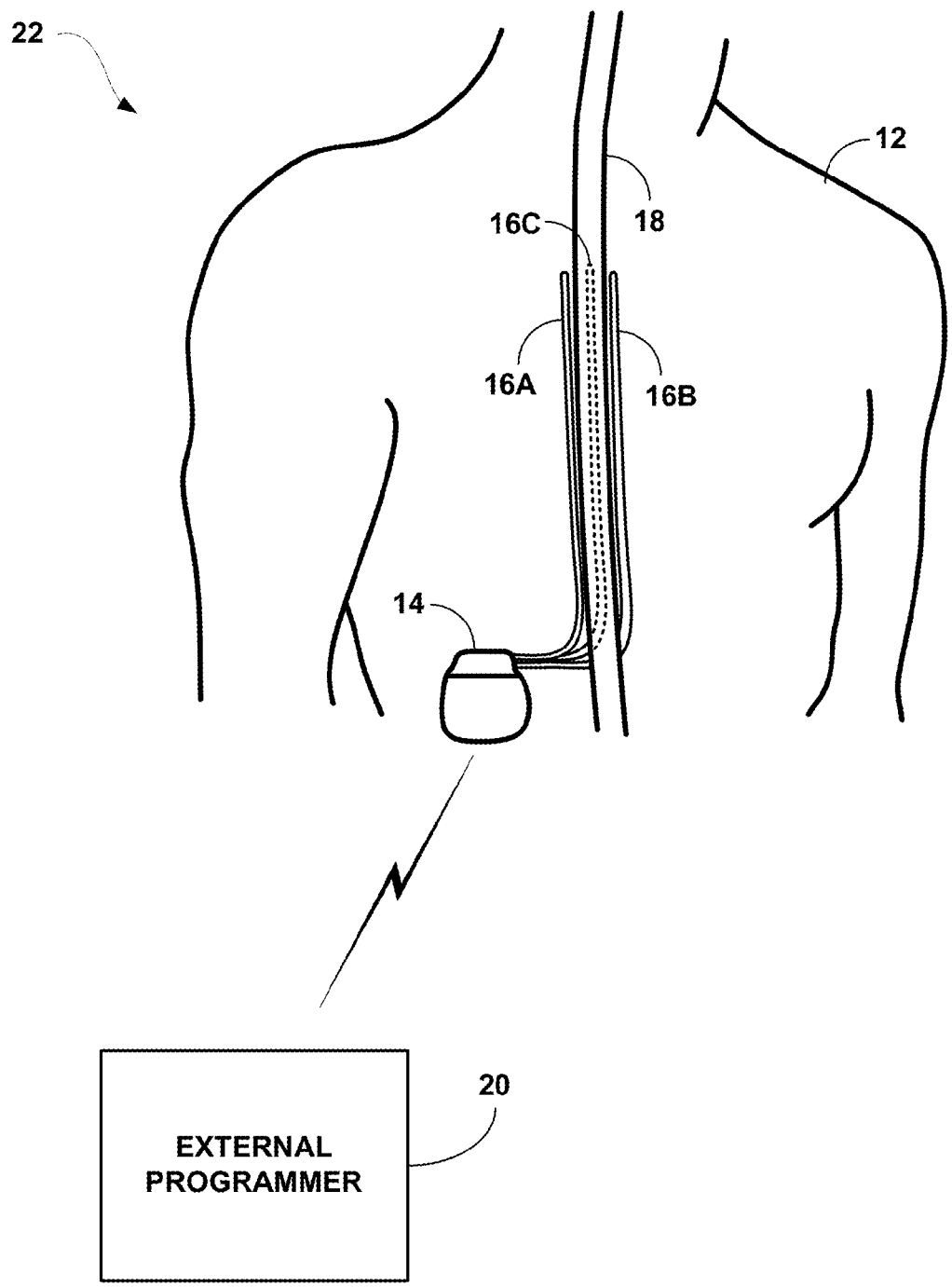
FIG. 2 is a conceptual diagram illustrating an example implantable stimulation system including three implantable stimulation leads.

FIG. 2 is a conceptual diagram illustrating an implantable stimulation system 22 including three implantable stimulation leads 16A, 16B, 16C (collectively leads 16). System 22 generally conforms to system 10 of FIG. 1, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 to allow programmer 20 to appropriately program stimulation therapy or assist in the programming of stimulation therapy.

In some examples, leads 16A and 16B each include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16A-16C. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 3:
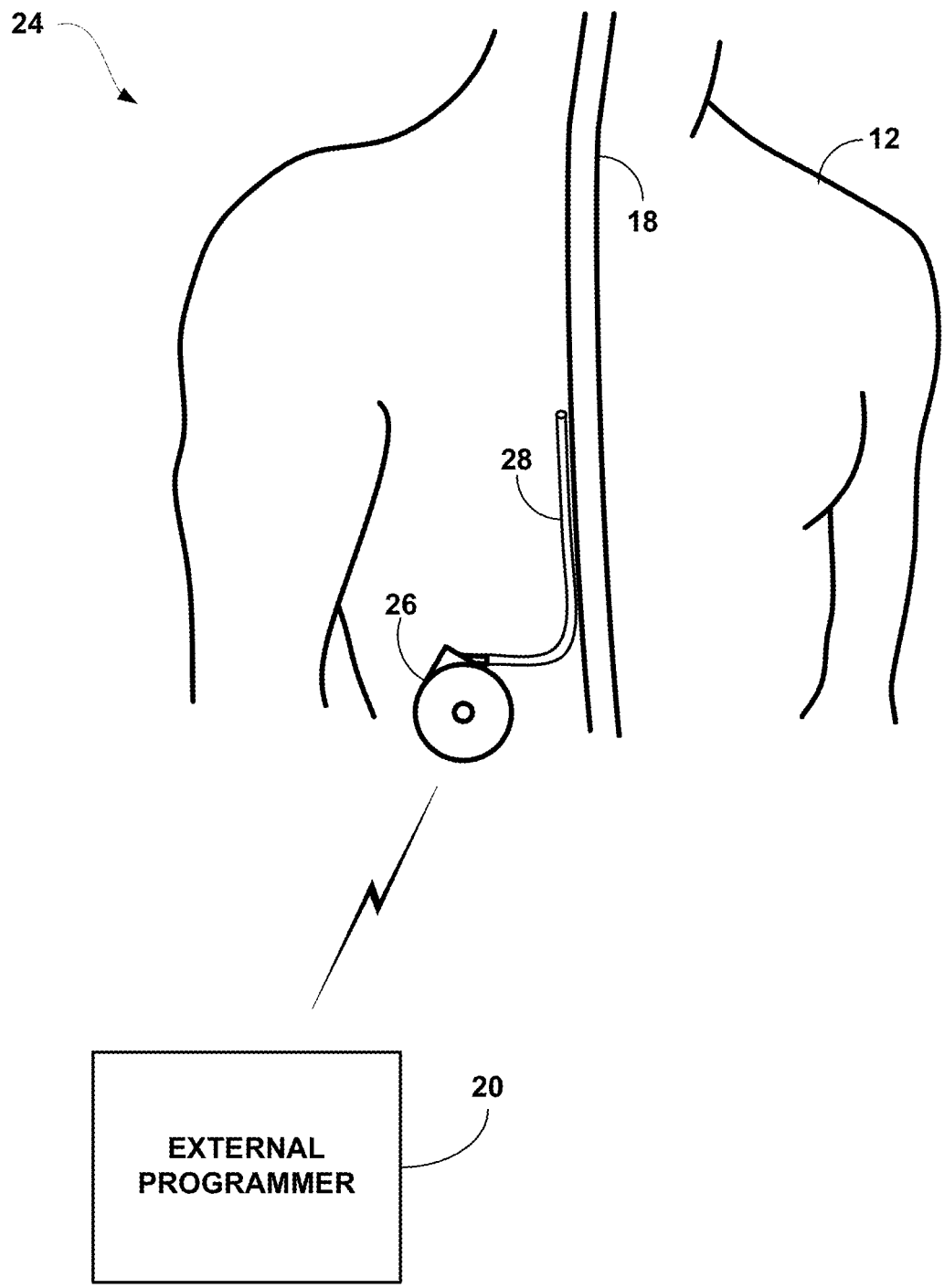
FIG. 3 is a conceptual diagram illustrating an example implantable drug delivery system including a delivery catheter.

FIG. 3 is a conceptual diagram illustrating an implantable drug delivery system 24 including one delivery catheter 28 coupled to IMD 26. As shown in the example of FIG. 3, drug delivery system 24 is substantially similar to systems 10 and 22. However, drug delivery system 24 performs the similar therapy functions via delivery of one or more therapeutic agents instead of electrical stimulation therapy. IMD 26 functions as a drug pump in the example of FIG. 3, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter to deliver a therapeutic agent to patient 12, e.g., in the same manner as catheter 28. Alternatively, the percutaneous catheter can be coupled to catheter 28, e.g., via a fluid coupler. In other examples, IMD 26 may include both electrical stimulation capabilities as described in IMD 14 (FIG. 1) and drug delivery therapy.

Figure 4:
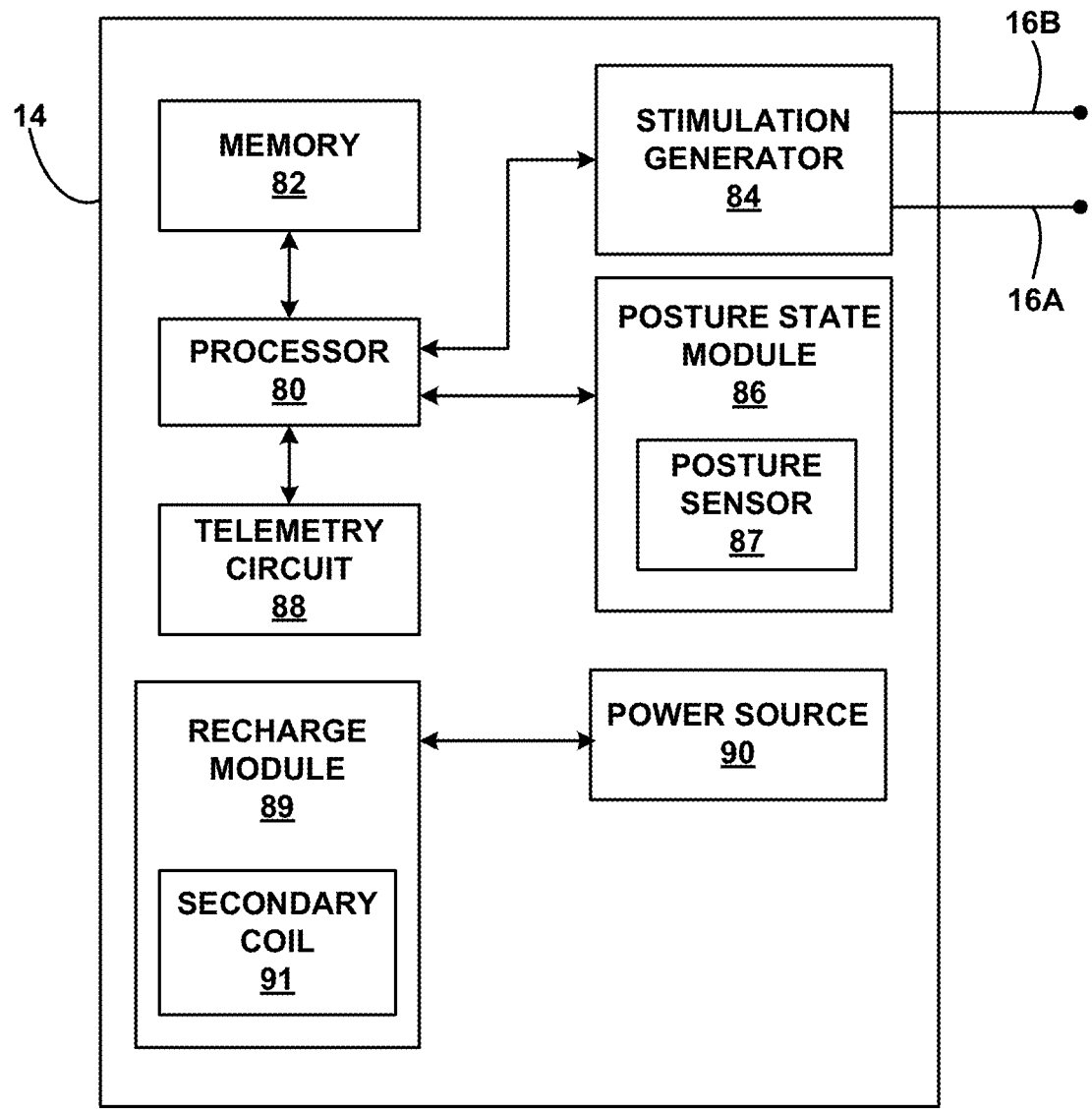
FIG. 4 is a functional block diagram illustrating various components of an example implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, recharge module 89, and power source 90. The stimulation generator 84 forms an example therapy delivery module.

Power source 90 may include a rechargeable power source that delivers power to the other components of IMD 14 to allow IMD 14 to operate as described in this disclosure. Power source 90 may be any of a variety of rechargeable power sources including a chemically-based battery or a capacitor. In one embodiment, rechargeable power source 90 includes a lithium ion battery. Any other type of rechargeable battery suitable for powering IMD 14 may be used according to the disclosure.

Periodically, the charge level of power source 90 may become depleted due the expenditure of energy by IMD 14. Recharge module 89 may be electrically coupled to power source 90, and configured to recharge power source 89 when depleted to some degree. The recharging of power source 90 may be accomplished through proximal inductive interaction between the primary coil of an external charger (e.g., programmer 20) and secondary charging coil 91 of recharge module 89. For example, recharge module 89 may include a secondary coil 91 which may be inductively coupled to primary coil 113 (FIG. 6) of programmer 20. Secondary coil 91 may be located partially or entirely within the housing of IMD 14 or may be located external to IMD 14 but electrically coupled to power source 90 within the housing of IMD 14, e.g., via one or more electrically conductive cables. When the primary coil of programmer 20 is placed in close proximately to secondary coil 91 of recharge module 89, an alternating current may be driven through the primary coil to induce a current in secondary coil 91 through inductive coupling. Recharge module 89 may use the induced current in secondary coil 91 to recharge power source 90.

Recharge module 89 may include one or more sensors configured to detect the current in and/or voltage across secondary coil 91 or power source 90, e.g., at one or more points during a recharge session. As will be described below, using such information, processor 80 or other processor may determine the recharge coupling efficiency at one or more points during a recharge session. Recharge module 89 may be configured to additionally or alternatively measure one or more other parameters that may be used to determine the recharge coupling efficiency at one or more points during a recharge session.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy data, posture state information (e.g., posture state definitions, information associating posture states with therapy programs, and the like), and any other information regarding therapy or patient 12.

Memory 82 may be considered, in some examples, a non-transitory computer-readable storage medium comprising instructions that cause one or more processors, such as, e.g., processor 80, to implement one or more of the example techniques described in this disclosure. The term "non-transitory" may indicate that the storage medium is not embodied in a carrier wave or a propagated signal. However, the term "non-transitory" should not be interpreted to mean that memory 82 is non-movable. As one example, memory 82 may be removed from IMD 16, and moved to another device. In certain examples, a non-transitory storage medium may store data that can, over time, change (e.g., in RAM).

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 to approximately 1200 Hz, such as between approximately 5 to approximately 250 Hz, or between approximately 30 to approximately 185 Hz, and a pulse width in the range of approximately 10 microseconds and approximately 5000 microseconds, such as between approximately 60 microseconds and approximately 1000 microseconds, or between approximately 60 microseconds and approximately 450 microseconds, or between approximately 60 microseconds and approximately 150 microseconds. Amplitude ranges such as those described above with reference to SCS, or other amplitude ranges, may be used for different DBS applications. Parameter values and ranges of values other than the example values described above are contemplated.

Processor 80 accesses stimulation parameters in memory 82, e.g., as programs and groups of programs. Upon selection of a particular program group, processor 80 may control stimulation generator 84 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to detect the patient posture state, e.g., posture, activity or any other static position or motion of patient 12. In the example of FIG. 4, posture state module 86 includes posture sensor 87 that generates one or more sensor signals that may be used to detect the posture state of patient 12. In some examples, posture sensor 87 may include one or more accelerometers, such as a three-axis accelerometer, capable of detecting static orientation or vectors in three-dimensions (e.g., x, y, z coordinate vectors). Example accelerometers may include a micro-electro-mechanical system (MEMS)-based accelerometer. In other examples, posture state module 86 may alternatively or additionally include posture sensor 87 in the form of one or more gyroscopes, piezoelectric crystals, pressure transducers or other sensors to sense the posture state of patient 12. Posture sensor data generated by posture state module 86 via posture sensor 87 and processor 80 may correspond to an activity and/or posture undertaken by patient 12 or a gross level of physical activity, e.g., activity counts based on footfalls or the like.

Posture sensor data from posture state module 86 may be stored in memory 82 for later review by a clinician, used to adjust therapy, present a posture state indication to patient 12 (e.g., via patient programmer 20) or some combination thereof. In one example, processor 80 may record one or more posture sensor values, or output, of the 3-axis accelerometer as posture sensor data during a recharge session. Additionally or alternatively, processor 80 may record the one or more posture states detected from the posture sensor output during the recharge session.

At the same time, processor 80 may record the recharge coupling efficiency during the recharge session. In some examples, processor 80 may determine the recharge coupling efficiency during a recharge session based on the current in, and/or voltage across, secondary coil 91 of recharge module 89. In some examples, processor 80 may compare the power associated with primary coil 113 (FIG. 6) of programmer 20 to that measured in secondary coil 91 of recharge module 89 to determine the efficiency of the power transfer during a recharge session. The recharge coupling efficiency determined during the recharge session may be associated on a temporal basis with the posture sensor data (e.g., the posture sensor output and/or posture state of patient 12) during the recharge session.

Using this information, processor 80 may determine, for example, the amount of time that patient 12 occupied respective posture states during a recharge session and/or the average recharge coupling efficiency observed for each respective posture state during the recharge session. Additionally or alternatively, processor 80 may determine the recharge coupling efficiency in response to the detection of one or more changes in the output of posture sensor 87 during a recharge session. Information from a single recharge session may be evaluated in such a manner or information from multiple recharge sessions may be combined and evaluated in such a fashion.

Memory 82 may include definitions for each posture state of patient 12 based on posture state reference data. In one example, the definitions of each posture state may be illustrated as a cone in three-dimensional space. Whenever the posture sensor data, e.g., a coordinate vector, from the three-axis accelerometer of posture state module 86 resides within a predefined cone defined by the posture state reference data, processor 80 indicates that patient 12 is in the posture state of the cone. In other examples, posture sensor data from the 3-axis accelerometer may be compared to a look-up table or applied to an equation to determine the posture state in which patient 12 currently resides.

As an illustration, to detect the posture state of a patient, processor 80 may receive posture sensor data generated by one or more posture sensors 87 and compare the posture sensor data to posture state reference data stored in memory 82. In the case of a posture state module including a three-axis accelerometer sensor, the posture sensor data generated by the one or more posture sensors may comprise a coordinate vector in a 3-dimensional space, e.g., as determined from the sensor signal values for each of the x, y, and z-axis. The posture state reference data may define a reference coordinate vector and a range of coordinates within a predetermined distance from the reference coordinate vector for the 3-dimensional space. In such a case, the posture state reference data may, in effect, define a posture volume or zone, such as, e.g., a posture cone. The posture cone, and the range of vector coordinates within the cone, may be defined in a variety of ways. For example, the posture cone may be defined by a distance or angle relative to the reference coordinate vector. As an alternative, a range of cosine values may define vectors within the cone in the sense that a cosine value computed for each of the vectors in the cone and the reference coordinate vector falls within the range of cosine values.

If processor 80 determines that the posture sensor data indicates a coordinate vector that falls within the range of coordinates defined by the posture state reference data for the 3-dimensional space, processor 80 may determine that the patient occupies the posture state associated with the posture state reference data. If the coordinate vector indicated by posture sensor data falls within the range of posture coordinates specified by the posture state reference data corresponding to an upright posture state, for example, then processor 80 may detect that the patient is in the upright posture state. Different posture states may be associated with different sets of posture state reference data. The posture sensor data may be compared to multiple sets of posture state reference data until a matching posture state is detected. In some examples, however, posture sensor data may fall within undefined areas that do not match any posture state reference data. In such cases, the IMD may detect that the patient is in an undefined posture state rather than a defined postures state.

In some examples, processor 80 may determine posture state reference data for one or more posture states of the patient by measuring the output signal values for each axis of an accelerometer sensor when the patient actually occupies the respective posture state. For example, while a patient occupies a standing posture state, the posture sensor reference data (e.g., x, y, and z axis values and/or vector magnitude) for the standing posture state may be defined based on the measured values for each output signal generated by the accelerometer sensor for each of the x, y, and z axis at that point in time. Examples techniques for defining and detecting patient posture state based on the output of one or more posture sensor include the examples described in U.S. Patent Application Publication No. 2010/0010383 by Skelton et al., titled "REORIENTATION OF PATIENT POSTURE STATES FOR POSTURE-RESPONSIVE THERAPY," which is incorporated herein by reference in its entirety.

IMD 14 may also store which group or program was being used to deliver therapy when patient 12 was in the sensed posture. Further, processor 80 may also adjust therapy for a new posture when posture state module 86 indicates that patient 12 has in fact changed posture states. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

Although posture sensor 87 is described in some instances as including a 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the posture state of patient 12 may be determined from multiple posture sensors placed at various locations on or within the body of patient 12.

In some examples, processor 80 processes the analog output of posture sensor 87 in posture state module 86 to determine activity and/or posture data. For example, where posture sensor 87 comprises an accelerometer, processor 80 or a processor of posture state module 86 may process the raw signals generated by posture sensor 87 to determine activity counts. In some examples, processor 80 may process the signals provided by the posture sensor 87 to determine velocity of motion information along each axis.

In one example, each of the x, y, and z axis signals generated by posture sensor 87 has both a DC component and an AC component. The DC components describes the gravitational force exerted upon sensor 87 and can thereby be used to determine orientation of the sensor within the gravitational field of the earth. Assuming the orientation of the sensor is relatively fixed with respect to the patient, the DC components of the x, y and z axis signals may be utilized to determine the patient's orientation within the gravitational field, and hence to determine the posture of the patient, assuming proper orientation of the sensor to the patient's body. The AC component of the x, y and z axis signals yields information about patient motion. In particular, the AC component of a signal may be used to derive a value for an activity describing the patient's motion. This activity may involve a level, direction of motion, or acceleration of the patient.

IMD 14 wirelessly communicates with external programmer 20, e.g., patient programmer 30 or clinician programmer 60, or another device by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Figure 5:
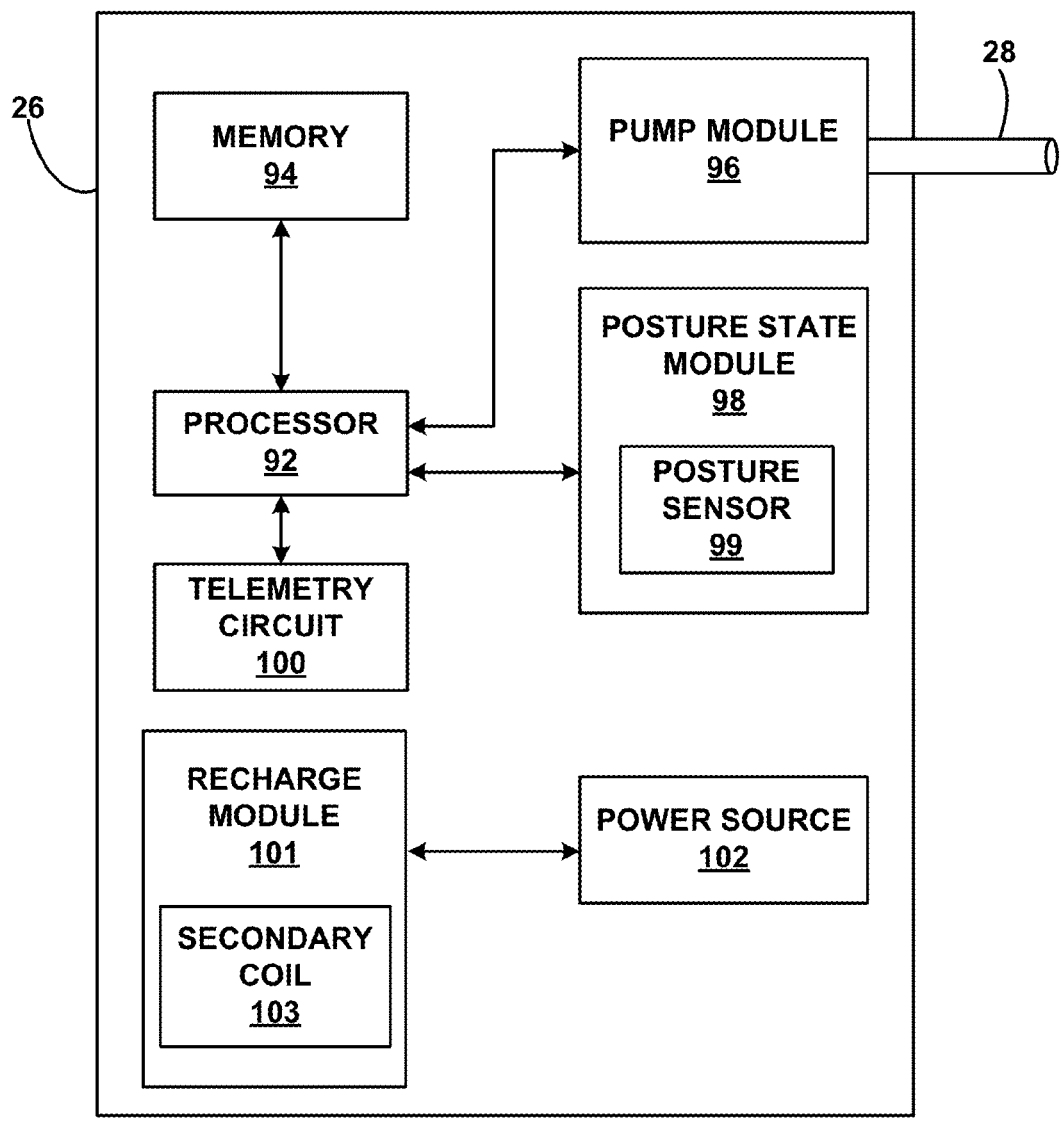
FIG. 5 is a functional block diagram illustrating various components of an example implantable drug pump.

FIG. 5 is a functional block diagram illustrating various components of an IMD 26, which delivers a therapeutic agent to patient 12. IMD 26 includes processor 92, memory 94, pump module 96, posture state module 98, telemetry circuit 100, recharge module 101, and power source 102. Posture state module 98 include posture sensor 99, and recharge module includes secondary coil 103. Similarly named features of IMD 26 may be substantially the same as that described for IMD 14. IMD 26 is a drug pump that operates substantially similar to IMD 14 of FIG. 4, but delivers a therapeutic agent rather than electrical stimulation. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts his or her posture.

Figure 6:
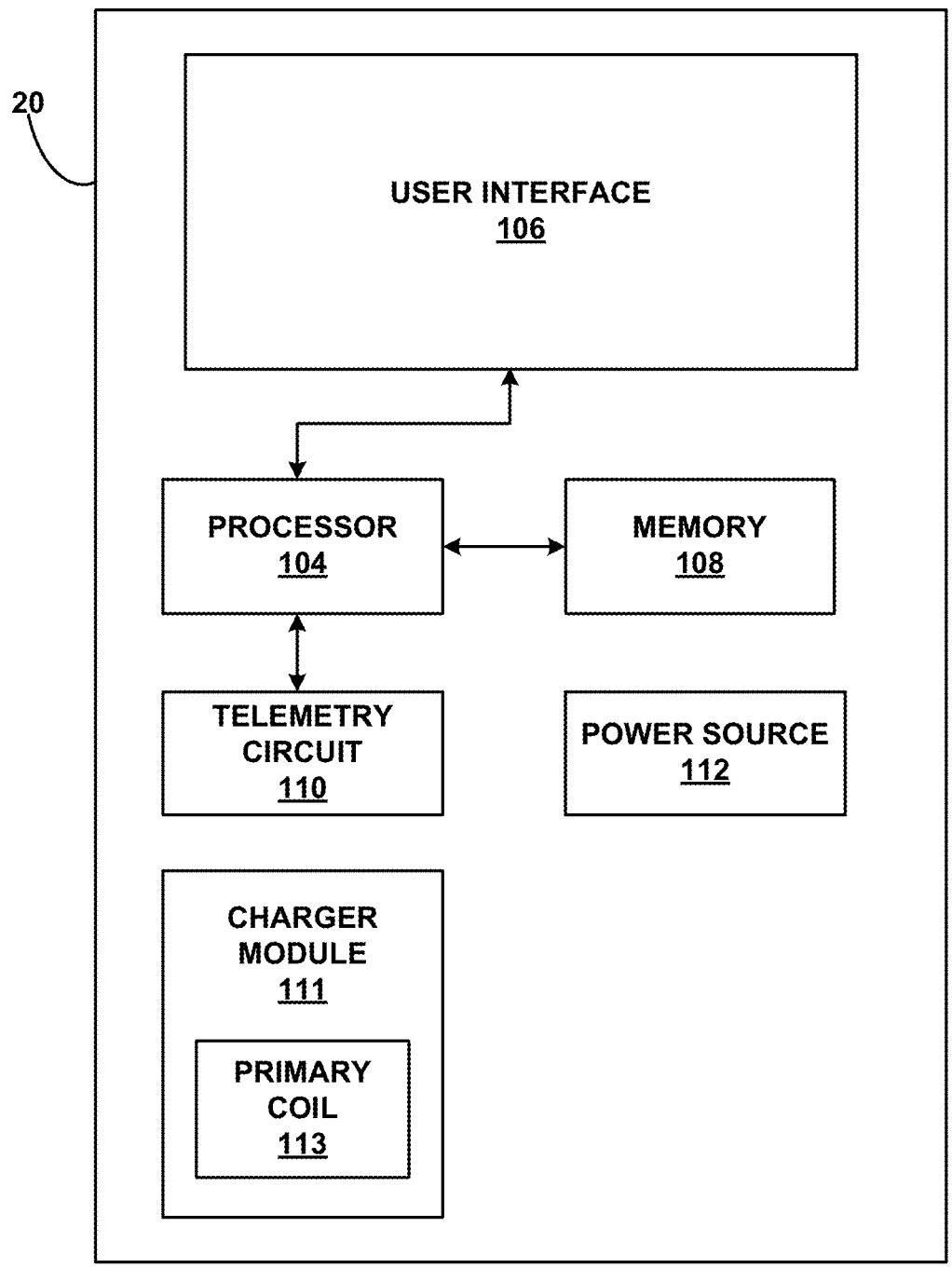
FIG. 6 is a functional block diagram illustrating various components of an example external programmer for an implantable medical device.

FIG. 6 is a functional block diagram illustrating various components of an external programmer 20 for IMDs 14 or 26. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 6, external programmer 20 includes processor 104, memory 108, telemetry circuit 110, user interface 106, charger module 111, and power source 112.

In some examples, external programmer 20 may be embodied as a patient programmer or a clinician programmer. External programmer 20 may provide a user interface 106 for a user, such as a patient 12, clinician, physician, technician, or nurse, to manage and program stimulation therapy. As a patient programmer, programmer 20 may accompany patient 12 throughout a daily routine. In some cases, programmer 20 may be used by a clinician when patient 12 visits the clinician in a hospital or clinic. In other examples, programmer 20 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Using programmer 20, a user may program stimulation therapy (e.g., selecting stimulation parameter values), modify programs or groups, retrieve stored therapy data, retrieve posture state information from an IMD or another device, define posture states and other activity information, or any other therapy related function. In addition, programmer 20 may be capable of communicating with a networked server in order to send or receive an email or other message, retrieve programming instructions, access a help guide, send an error message, or perform any other function that may be beneficial to prompt therapy.

Processor 104 processes instructions by memory 108 and may store user input received through user interface 106 into the memory when appropriate for the current therapy. In addition, processor 104 provides and supports any of the functionality described herein with respect to each example of user interface 106. Processor 104 may comprise any one or more of a microprocessor, DSP, ASIC, FPGA, or other digital logic circuitry, and the functions attributed to programmer 104 may be embodied as software, firmware, hardware or any combination thereof.

Memory 108 may include any one or more of a RAM, ROM, EEPROM, flash memory or the like. Memory 108 may include instructions for operating user interface 106, telemetry module 110 and managing power source 112. Memory 108 may store program instructions that, when executed by processor 104, cause processor 104 and programmer 20 to provide the functionality ascribed to them herein. In some examples, memory 108 may store information for one or more therapy programs used to define therapy delivered from IMD 14 to patient 12. Additionally or alternatively, therapy program information may be stored in memory 82 of IMD 14. Memory 108 also includes instructions for generating and delivering programming commands to IMD 14, such as a programming command that instructs IMD 14 to activate or deactivate a posture-responsive therapy mode. Memory 108 may also include a removable memory portion that may be used to provide memory updates or increases in memory capacities. A removable memory may also allow patient data to be easily transferred to another computing device, or to be removed before programmer 20 is used to program therapy for another patient.

Memory 108 may be considered, in some examples, a non-transitory computer-readable storage medium comprising instructions that cause one or more processors, such as, e.g., processor 104, to implement one or more of the example techniques described in this disclosure. The term "non-transitory" may indicate that the storage medium is not embodied in a carrier wave or a propagated signal. However, the term "non-transitory" should not be interpreted to mean that memory 108 is non-movable. As one example, memory 108 may be removed from programmer 20, and moved to another device. In certain examples, a non-transitory storage medium may store data that can, over time, change (e.g., in RAM).

A clinician, patient 12, or another user (e.g., a patient caretaker) interacts with user interface 106 in order to manually change the stimulation parameter values of a program, change programs within a group, turn posture-responsive stimulation ON or OFF, view therapy information, view posture state information, or otherwise communicate with IMDs 14 or 26.

User interface 106 may include a screen and one or more mechanisms, such as, buttons, as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like.

Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

External programmer 20 may include charger module 111 configured to recharge a power source, such as a rechargeable battery or capacitor of power source 90 of IMD 14. In the example shown in FIG. 6, programmer 20 may integrate programming components with recharging components to form a combined programmer/recharger unit. While a combined programmer/recharger unit is described in the disclosure, in other examples, charger module 111 and other charger components may be embodied in an external device primarily used to recharge power source 90 of IMD 14 that is separate from the of an external device configured primarily for the programming of IMD 14.

Charger module 111 of programmer 20 is configured to recharge a rechargeable power source, such as, power source 90 of IMD 14, via inductive energy transfer. Charger module 111 includes primary coil 113. In some examples, primary coil 113 is located external to the housing of programmer 20 and electrically coupled to power supply 112 and other components of programmer 20 via one or more wires. In such a configuration, patient 12 may be able to position and reposition primary coil 113 relatively independently (subject primarily to the constraints of any coupling wires) of programmer 20, e.g., during a recharge session. In an alternative embodiment, primary coil 113 may be partially or entirely contained within the housing of programmer 20.

During a recharge session, power source 112 generates an alternating current in primary coil 113 of charger module 111. When primary coil 113 of charger module 111 is positioned proximate to secondary coil 91 of recharge module 89, the current in primary coil 113 inductively couples primary coil 113 to secondary coil 91. For example, the magnetic field generated by the flow of current in primary coil 113 acts on secondary coil 91 to generate a current in secondary coil 91. The resulting current in secondary coil 91 is employed by recharge module 89 to recharge rechargeable power source 90 of IMD 14.

Power source 112 may include batteries to power recharge module 89 to drive primary coil 113 such that patient 12 may be somewhat ambulatory or otherwise able to move around while charging IMD 14. In such an example, a desktop recharging system (not shown) which is coupled to an AC or DC power source may be periodically coupled to programmer 20 to recharge power source 112 of programmer 20. In another example, programmer 20 may be coupled via a power cord to a source of AC power, such as a standard wall outlet, to generate a current in primary coil 113 during a recharge session.

During a recharge session, patient 12 or other user may position primary coil 113 externally relative to secondary coil 91 of IMD 14 as implanted in patient 12. Patient 12 may locate primary coil 113 relative to secondary coil 91 in a position that allows for a desired level of recharge coupling efficiency, e.g., based on feedback from module 89 to module 111 with regard to the coupling between secondary and primary coils 91, 113. In some examples, primary coil 113 may be embodied in a form that allows primary coil 113 to be affixed to patient 12 in a desired position. For example, primary coil 113 may be included in a belt or other device that may temporally strapped around torso, waist, or part of patient 12 with primary coil 113 in a desired position. Alternatively, primary coil 113 may take the form of an adhesive patch that may be temporarily adhered to the skin or clothing of patient 12 in a desired position. Other examples are contemplated.

Primary coil 113 and second coil 91 may take any suitable shape and size, and may have substantially the same or different size and shape. For instance, both coils 113 and 91 may be generally circular, both may be rectangular, one may be circular and the other rectangular, or either or both of the coils may be of a different shape. Either coil may be larger than the other, or the coils may be the same size.

The recharge coupling efficiency during a recharge session may be influenced by the location of secondary coil 91 relative to primary coil 113. Further, as is discussed above, in some instances, the recharge coupling efficiency may vary during a recharge session due to the movement of secondary coil 91 relative to primary coil 113 (e.g., movement that results in changes to the distance and/or angle between the primary and secondary coils). For example, the movement of patient 12 (e.g., a transition from one posture state to another) may cause secondary coil 91 to move relative to primary coil 113. In some examples, the recharge coupling efficiency exhibited when a patient occupies a particular posture state (e.g., reclining) may be greater than that of another posture state (e.g., upright). In such a case, it may be beneficial to identify one or more posture states of a patient that provide for a relatively high level of recharge coupling efficiency so that patient 12 may make an effort to occupy such a posture state during a recharge session. Similarly, it may be beneficial to identify one or more posture states of a patient that provide for a relatively low level of recharge coupling efficiency so that patient 12 may make an effort to avoid such posture states during a recharge session.

As described above, some examples of the disclosure relate to techniques for associating recharge coupling efficiency during a recharge session with posture sensor data generated during the recharge session. The posture sensor data may be indicative of the one or more posture states occupied by a patient during a recharge session. In some examples, the association of the recharge coupling efficiency with posture sensor data may be reviewed by a user to identify one or more posture states that correspond to recharging at a relatively high efficiency/rate, and/or one or more posture states that correspond to recharging at a relatively low efficiency/rate. Such information may allow a clinician to train or give feedback to patient 12 with respect to the posture state behavior of patient 12 during a recharge session (e.g., what postures state(s) to occupy and/or what posture state(s) to avoid). If the associated recharge coupling efficiency/posture sensor data reflects that the recharge coupling efficiency is relatively independent of the posture state of the patient, such information may be used to illustrate to patient 12 and others that patient movement and posture state may have substantially no influence on the recharge process for therapy system 10.

Figure 7:
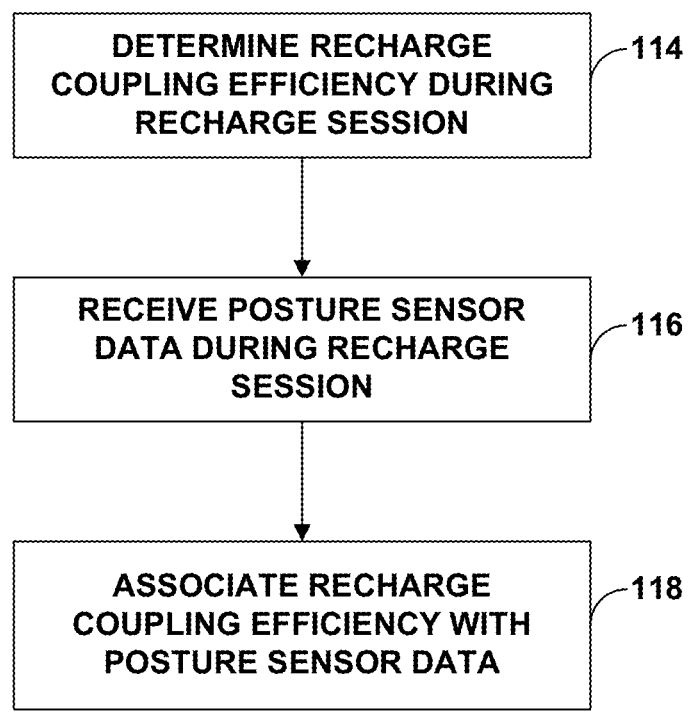
FIG. 7 is a flow diagram illustrating an example technique that may be employed while recharging a rechargeable power source of an example IMD.
Figure 8:
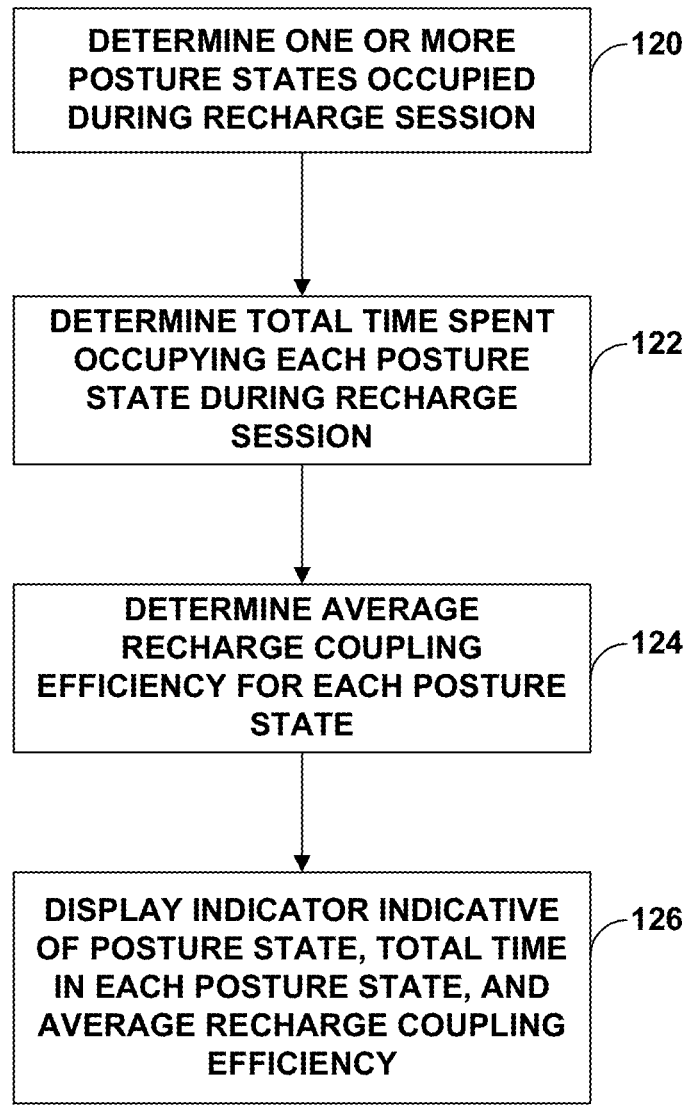
FIG. 8 is a flow diagram illustrating another example technique that may be employed while recharging a rechargeable power source of an example IMD.
Figure 10:
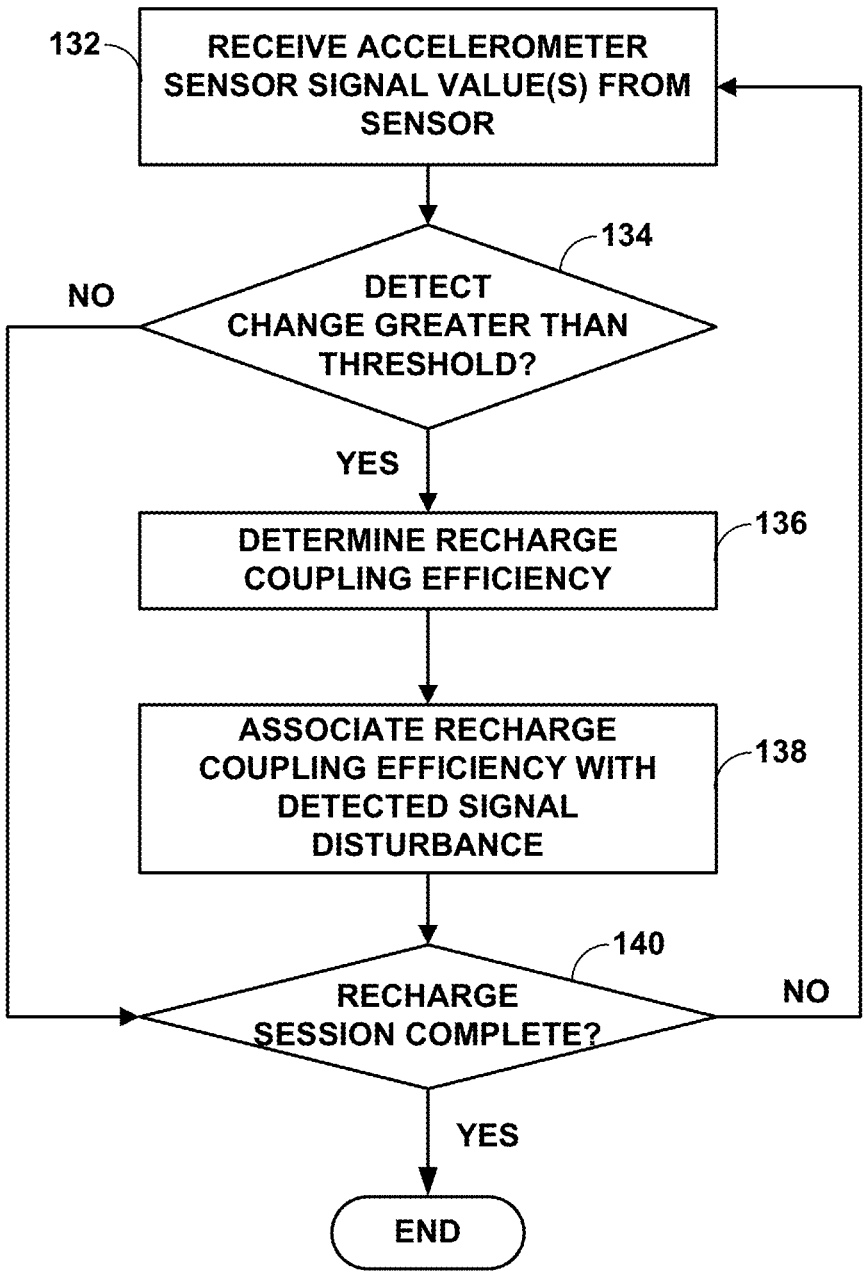
FIG. 10 is a flow diagram illustrating another example technique that may be employed while recharging a rechargeable power source of an example IMD.

FIG. 7 is a flow diagram illustrating an example technique that may be employed while recharging an example rechargeable power source of an IMD. For ease of illustration, the example technique of FIG. 7, as well as that of FIGS. 8 and 10, are described with regard to therapy system 10 (FIG. 1). However, such an example may be employed by any suitable system including an IMD with a rechargeable power source. Moreover, while the example of FIG. 7 is described as being performed by processor 80 of IMD 14, in other examples, processor 104 of programmer 20 and/or a processor of another device may perform all or a part of the example technique shown in FIG. 7.

As shown in FIG. 7, processor 80 may determine the recharge coupling efficiency at one more points during a recharge session (114). Initially, primary coil 113 of programmer 20 may be positioned by patient 12 relative to second coil 91 of IMD 14. In some cases, patient 12 may be guided to a particular location on, or near, his or her skin based on feedback provided by programmer 20. In other examples, patient 12 may position primary coil 113 based on instructions from a clinician or to correspond to a position used during one or more prior recharge sessions. During a recharge session, energy may be transferred from primary coil 113 to secondary coil 91 as described above, which may be used to recharge power source 90 of IMD 14. As noted above, the position of primary coil 113 relative that of secondary coil 91 influences the recharge coupling efficiency for the energy transferred transcutaneously from primary coil 113 to secondary coil 91. In general, the greater the recharge coupling efficiency between the primary coil 113 and secondary coil 91, the greater the rate of recharge of power source 90.

During the recharge session, processor 80 may also receive posture sensor data generated by postures sensor 87 (116). As described above, posture sensor 87 may include one or more accelerometer sensors whose output signals may be indicative of the posture state of patient 12. In the case of a three-axis accelerometer, the posture sensor data received by processor 80 may include raw or processed signal output values for one or more axes of posture sensor 89 generated during all or a portion of a recharge session. In some examples, the posture sensor data may include a magnitude for a coordinate vector determined from such signal output values. Additionally or alternatively, the posture sensor data received by processor 80 may include the one or more posture states occupied by patient 12, as detected based on the signals output of posture sensor 89, during all or a portion of the recharge session.

Processor 80 may associate the recharge coupling efficiency determined during the recharge session with the posture sensor data generated during the recharge session (118). Processor 80 may make the association on a temporal basis, e.g., such that the recharge efficiency during a particular point or period of time is associated with the posture sensor data for substantially the same point or period of time. In some examples, processor 80 may associate the recharge coupling efficiency and a posture sensor data by populating one or more data structures stored in memory 82 of IMD 14. For example, processor 80 may determine the recharge coupling efficiency and the current posture state at regular intervals (e.g., approximately 1 minute intervals) during a recharge session, and store the information in memory 82. In such an example, the memory structure may contain an initial timestamp, then a series of records after that where each record has two values: the recharge coupling efficiency value and the detected posture state. When later evaluated by processor 80, timing may be determined based on the fact that each record is separated by a minute.

In another example, processor 80 may store a histogram of determined posture states and recharge coupling efficiency in memory 82, e.g., with a memory structure as a 2-D array. In such an example, for a recharge session there would be a row for each posture state and a column for each recharge coupling efficiency value. Then each minute (or some other regular time interval), processor 80 may check the current posture state of patient 12 and the current recharge coupling, and then increment the counter in the cell that corresponds to that combination of posture state and coupling efficiency. Processor 80 may later read this information and display it directly as a histogram. Each posture state may have its own histogram of recharge coupling efficiency. The x-axis of the histogram may represent recharge coupling efficiency and the y-axis would be the number of minutes spent at each coupling level when in that posture state. In some examples, the y-axis may be in absolute minutes. In other example, the y-axis may be in percentage of time, where the percentage of time could be determined by dividing the number of minutes at a particular recharge coupling efficiency value by the total number of minutes in that posture state.

Processor 80 may associate the recharge coupling efficiency and posture sensor data with each other during the recharge session (118). In other examples, the information may be separately recorded and stored in memory 82, and accessed at a later time by processor 80 for association with each other. In some examples, processor 80 may store the posture sensor data and/or recharge coupling efficiency during a recharge session in an ongoing fashion, e.g., loop recording. In some examples, information used to determine recharge coupling efficiency (e.g., measured current and/or voltage) may be stored in memory 82 and later accessed and processed by processor 80 to determine recharge coupling efficiency during the recharge session based on the stored information.

In some examples, each time patient 12 changes posture states, processor 80 may record the timestamp, the new posture state, and data used to determine the recharge coupling efficiency while occupying the posture state in a log in memory 82. In this way, the log of all the recharge data associated with posture state changes may be created by IMD 14 and then later retrieved for by programmer 20, e.g., during subsequent programming session, for analysis. Again, although some example techniques described in the disclosure are described primarily with regard to processor 80 of IMD 14, one or more other processors (e.g., processor 104 of programmer 20) may perform all or portion of the example techniques.

Processor 80 may determine the recharge coupling efficiency at one or more points during a recharge session using one or more suitable techniques (114). In some examples, processor 80 may measure the current within secondary coil 91 or entering power source 90 at a point or over a period of time and compare the measured current to a reference current value to determine the recharge coupling efficiency. In some examples, the reference current value may be the current measured in primary coil 113 of programmer 20 at substantially the same time as that of the current measure in secondary coil 91. In other examples, the reference current value may be an estimate of the current in primary coil 113 when the current in secondary coil 91 is measured, e.g., based on some previous measurement.

Based on the measured current and reference current, the percentage or ratio of current transferred from primary coil to secondary coil may be used to determine the recharge coupling efficiency. For example, such a value may be calculated by determining the current associated with each of the primary coil 113 and the secondary coil 91, and then dividing the latter by the former. In such cases, the recharge coupling efficiency may be expressed in terms of a percentage or ratio. However, other examples are contemplated in which recharge coupling efficiency is expressed in different terms, such as, e.g., as numeric or alphabetical rating, low/medium/high rating system, color coded ratings, actual current levels, and the like.

In other examples, the recharge coupling efficiency may be expressed only as the current measured within secondary coil 91 or entering power source 90. For example, measured current values may be used to represent recharge coupling efficiency in cases in which the current within primary coil 113 is generally assumed to be substantially constant. Additionally, expressing the recharge coupling efficiency as the current measured within secondary coil 91 or entering power source 90 may allow for the evaluation of two or more recharge coupling efficiencies relative to each other. For example, a comparison of the current measured while patient 12 occupies a first posture state to the current measured while patient 12 occupies a second posture state may reflect the relative recharge coupling efficiency with regard to the first and second posture states.

Similar techniques to those above for determining recharge coupling efficiency with regard to current may be used by measuring the voltage across secondary coil 91 and/or primary coil 113. Further, in some examples, the current in and voltage across both primary coil 113 and secondary coil 91 may be measured, e.g., by programmer 20 and IMD 14, respectively. Based on the measured current and voltage, the percentage or ratio of power transferred from primary coil to secondary coil may be used to determine the recharge coupling efficiency. For example, such a value may be calculated by determining the power associated with each of the primary coil 113 and the secondary coil 91, and then dividing the latter by the former. Other types of calculations or processing beyond that described may be performed if a different metric is selected for use as the recharge coupling efficiency value.

Processor 80 may determine the recharge coupling efficiency values during a recharge session on a substantially continuous or periodic basis. In some examples, processor 80 may determine a recharge coupling efficiency value at a frequency preprogrammed by a clinician or other authorized user. For example, processor 80 may determine the recharge coupling efficiency at a frequency of approximately 1 minute or approximately 5 minutes during a recharge session. Additionally or alternatively, processor 80 may determine the recharge coupling efficiency based on the detection of certain power source voltage measurement and/or temperature of IMD 14.

For a given period of time, the recharge coupling efficiency value may be based on a plurality of recharge coupling efficiency values determined during that period of time. For example, the recharge coupling efficiency over a period of time may be expressed as the average recharge coupling efficiency of a plurality of recharge coupling efficiency values determined by processor 80 during the period of time.

As will be described below, in some examples, processor 80 may determine the recharge coupling efficiency at one or more points during a recharge session in response to the detection of one or more variations in the posture sensor data generated by posture sensor 89. Such variations may correspond to a transition in patient posture state and/or mechanical force applied to IMD 14.

Processor 80 may determine the recharge coupling efficiency during substantially all or only a portion of a recharge session (114). To temporally associate the recharge coupling efficiency with the received posture sensor date, processor 80 may determine the recharge coupling efficiency (or at least record the information used to determine the recharge coupling efficiency at a later point) over substantially the same time as the posture sensor data is generated by posture sensor 89. In this manner, the association of the recharge coupling efficiency during a recharge session with posture sensor data generated during the recharge session may allow processor 80 and/or a user to identify the existence of one or more relationships between the posture state behavior of patient 12 and recharge coupling efficiency during all or a portion of a recharge session.

FIG. 8 is a flow diagram illustrating another example technique that may be employed while recharging rechargeable power source 90 of IMD 14. For ease of illustration, the example of FIG. 8 is described as being performed by processor 104 of programmer 20, in other examples, processor 80 of IMD 14 and/or a processor of another device may perform all or a part of the example technique shown in FIG. 8.

As shown in FIG. 8, processor 104 may determine the one or more posture states occupied by patient 12 during a recharge session (120). Processor 104 may determine the one or more posture states based on the posture state data received during the recharge session (116). In one example, processor 104 may determine that patient 12 occupied a single posture state (e.g., lying) throughout the entire recharge session based on the output of posture sensor 89 received during the recharge session. In other examples, processor 104 may determine that patient 12 occupied at least two different posture states (e.g., both lying and reclining) during a recharge session based on the output of posture sensor 89 received during the recharge session. In some cases, processor 104 may determine that patient 12 occupied the same posture state more than once during a recharge session, e.g., if patient 12 transitions out of a first posture state to a second posture state and then returns to the first posture state at some later point during the same recharge session. Processor 104 may receive the posture state information in or near real time from IMD 14 or at some later time, in which case IMD 14 may store the received information for a period of time in memory 82.

For each posture state determined by processor 104 (120), processor 104 may also determine the amount of time that patient 12 spent occupying the posture state (122). If patient 12 occupies a single posture state during recharge session, processor 104 may determine that total time occupying that posture state is substantially equal to that of the duration of the recharge session. If patient 12 occupies multiple posture states during a recharge session, processor 104 may track the amount of time spent in each posture state. Additionally, for recharge sessions in which patient 12 occupies substantially the same posture state more than once during the same recharge session, processor 104 may determine the amount of time occupying the respective posture state for each instance and/or in total during the recharge session.

Additionally, for each posture state determined by processor 104 (120), processor 104 may determine the average recharge coupling efficiency detected while patient occupied the posture state (124). For example, in a case in which patient 12 occupies the same posture state throughout a recharge session and recharge coupling efficiency is expressed in terms of a ratio of the current of secondary coil 91 to the current of primary coil 113, the average recharge coupling efficiency may be based on the current values sampled throughout the recharge session. For recharge sessions in which patient 12 occupies multiple posture states, processor 104 may determine the average recharge coupling efficiency for each posture state based the current values sampled when patient occupied respective posture states. For example, for a recharge session in which processor 104 determines that patient 12 occupied both an upright posture state and reclining posture state, processor 108 may determine the average recharge coupling efficiency based on the current values sampled while the received posture state data indicated that patient 12 was upright during the recharge session. Likewise, processor 108 may determine the average recharge coupling efficiency based on the current values sampled while the received posture state data indicated that patient 12 was reclining during the recharge session.

While processor 104 determines the average recharge coupling efficiency in the example of FIG. 7, in other examples, processor 104 may determine some other statistically significant value representative of the recharge coupling efficiency determined during the time period patient 12 occupied a particular posture state. For example, processor 104 may determine the median, standard deviation, and/or mean of recharge coupling efficiency for a posture state, and/or weighted average over several postures.

Processor 104 may then generate and display an indicator indicative of one or more of the posture states occupied during a recharge session, total time occupied in each displayed posture state, and average recharge coupling efficiency during each displayed posture state via user interface 106 (126). In some examples, the indicator may include one or more graphical indicators, e.g., in the form of texts and/or graphs, indicative of each of the described parameters. In some examples, the indicator may simply be table listing the total time and average recharge efficiency for each detected patient posture state during the recharge session. In some examples, a textual display or other type of indicator may be used to indicate one or more of the posture states occupied during a recharge session, the total time spent in each posture state, the average recharge coupling efficiency for each posture state, the average coupling efficiency during a recharge session, and/or the overall duration of a recharge session. Processor 104 may display multiple indicators substantially simultaneously or separately via user interface 106. Example indicators other than those examples shown and described are contemplated.

In some examples, the example indicator may allow user to identify one or more relationships that existed between the patient posture state behavior and recharge coupling efficiency during a recharge session. For example, an example indicator displayed by programmer 20 via user interface 106 may be reviewed by a user to identify one or more posture states that correspond to recharging at a relatively high recharge coupling efficiency/recharge rate and/or one or more posture states that correspond to recharging at a relatively low recharge coupling efficiency/recharge rate. Such information may allow a clinician to train or give feedback to a patient with respect to the posture state behavior of a patient during a recharge session (e.g., what postures state(s) to occupy and/or what posture state(s) to avoid). Moreover, if the associated recharge coupling efficiency/posture sensor data reflects that recharge coupling efficiency is relatively independent of the posture state of the patient, such information may be used to illustrate to patient 12 and others that patient movement and posture state may have substantially no influence on the efficiency of the recharge process for therapy system 10. In some instances, when displayed, such information may be used as a diagnostic tool when troubleshooting issue with the process used to recharge the power source 90 of IMD 14.

While the example of FIG. 8, as well as the other examples of the disclosure, are described primarily with regard to a single recharge session, such techniques may also be used to evaluate data generated during all or a portion of multiple separate recharges sessions. For example, recharge coupling efficiency may be associated with posture sensor data (e.g., posture state), as described, for multiple recharge sessions. The data from multiple sessions may be combined (e.g., on the basis of posture state) to reflect the temporal relationship between recharge coupling efficiency and posture state data over the course of the multiple recharge sessions. This data may be updated dynamically as additional recharge sessions occur over time. In some examples, rather than combining the data, that data from multiple sessions may be analyzed individually to allow for evaluation of recharge coupling efficiency and posture state data for respective recharge sessions relative to each other. Such an approach may be used to illustrate changes in the behavior of patient 12 during recharge sessions from one session to another, e.g., after an attempt has been made to tailor his or her behavior based the review of recharge coupling efficiency and posture state data from earlier recharge sessions.

Figure 9:
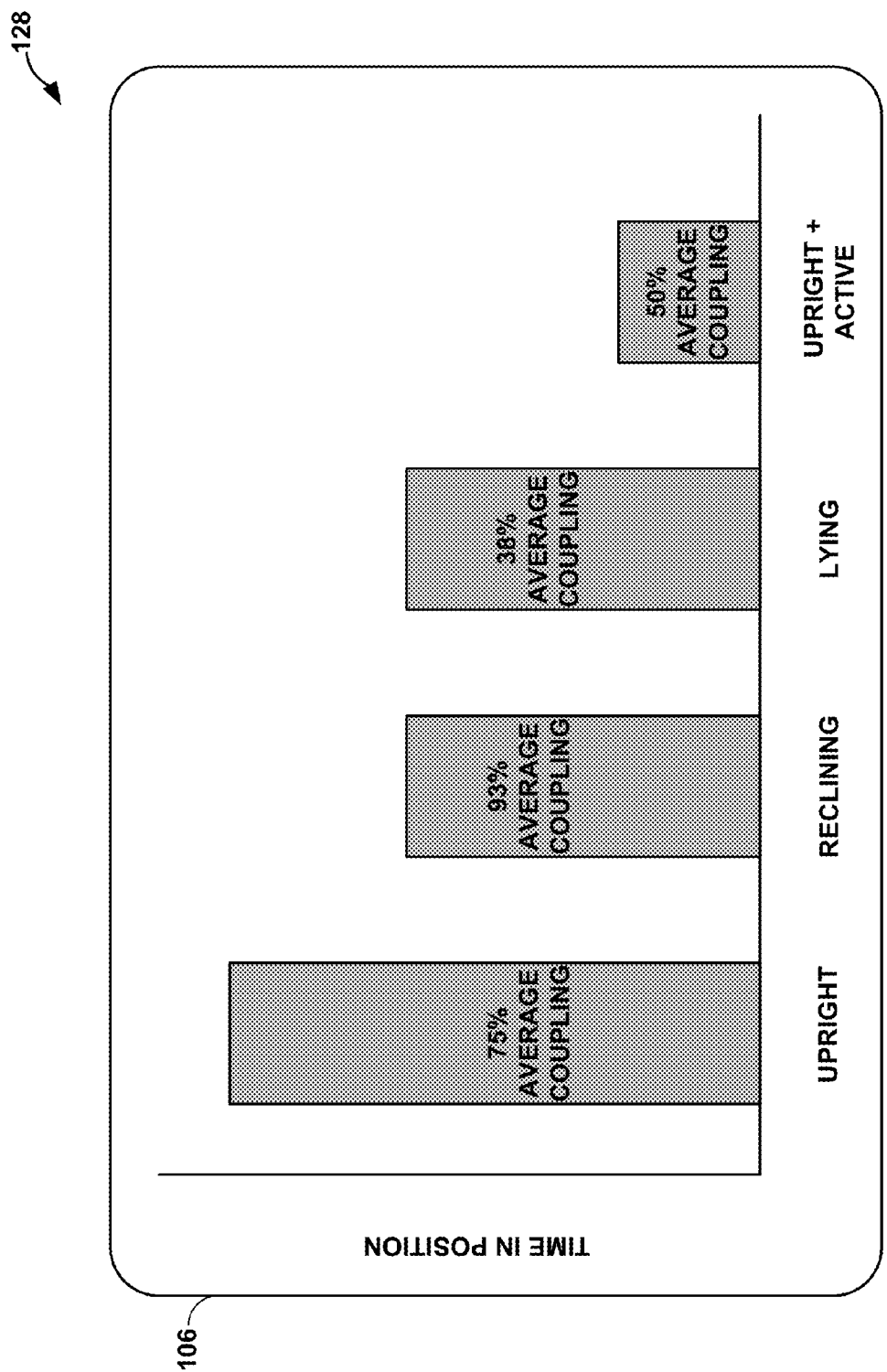
FIG. 9 is a conceptual diagram illustrating an example screen that may be displayed by an example external display device.

FIG. 9 is a conceptual diagram illustrating an example screen 128 that may be displayed on a display, such as, e.g., a display of user interface 106 of programmer 20. Screen 128 is an example of a graphical indicator indicative of the information determined in the example of FIG. 8. In particular, screen 128 includes a bar graph indicating the relative amount of time spent in a posture state along the vertical axis for each posture state labeled on the horizontal axis. In the example shown, the posture state data during one or more recharge sessions indicated that patient 12 occupied upright, reclining, lying, upright and active posture states. These four posture states may be the only posture states occupied by patient 12 during a recharge session or patient 12 may have occupied one or more other posture states during the recharge session which are not indicated on screen 128.

As shown, screen 128 indicates that, during the recharge session in question, patient 12 occupied an upright posture state for the most time out of the four posture states, spent approximately the same amount of time in reclining and lying posture states, and spent the least amount of time in an upright and active posture state. Patient 12 may have only occupied each of the respective posture states once during the recharge session or may have occupied one or more of the posture state during multiple different periods of time during the recharge session separated by periods occupying one or more different posture states.

Screen 128 also includes text within each respective bar indicating the average recharge coupling efficiency determined for the corresponding posture state. In particular, screen 128 indicates that processor 104 determined that the average recharge coupling efficiency was approximately 75% during the time that patient 12 occupied an upright posture state, the average recharge coupling efficiency was approximately 93% during the time that patient 12 occupied a reclining posture state, the average recharge coupling efficiency was approximately 38% during the time that patient 12 occupied a lying posture state, and the average recharge coupling efficiency was approximately 50% during the time that patient 12 occupied an upright and active posture state. In some examples, recharge coupling efficiency may be indicated using non-textual indicators. For example, a color coding scheme may be used in which the bar corresponding to a posture state may be filled in green if the average recharge coupling efficiency for that posture state was determined to be "good," filled in yellow if the average recharge coupling efficiency for that posture state was determined to be "fair,", and filled in red if the average recharge coupling efficiency for that posture state was determined to be "poor." In such a case, each one of "good," "poor," and "fair" may correspond to a predefined range of average recharge coupling percentage values.

In some examples, the horizontal sequence of respective posture states shown in screen 128 may temporally reflect the posture states occupied by patient during a recharge session. For example, as shown in FIG. 9, screen 128 may reflect a sequence in which patient 12 occupied an upright posture state, a reclining posture state, a lying posture state, and an upright and active posture state, in that order, during a recharge session. In other examples, an indicator indicating the sequence of patient posture states occupied by patient may be generated and displayed by screen 128 separately.

In some examples, screen 128 may also indicate time of day along with the detected posture state of patient 12 and other information, such as, recharge coupling efficiency. Such time to day information may be stored by processor 80 along with posture sensor data and recharge coupling efficiency in memory 82 during a recharge session. The time of day a patient occupies a posture state may further detail the actual posture state of patient 12. For example, in some case, posture sensor data generated when patient 12 is sitting upright may be substantially the same or similar to that generated while patient 12 is standing upright. Accordingly, the time of day information along with the posture sensor information may further help a clinician or other user identify the actual posture state of patient (e.g., patient 12 may be more likely to be seated in the morning when upright and standing in the evening when upright), and then relate the actual posture state of patient 12 the recharge coupling efficiency for the posture state.

A clinician, patient 12, or other user may view the information indicated by screen 128 after one or more recharge sessions. As noted above, in some examples, such information may allow user to identify one or more relationships that existed between the patient posture state behavior and recharge coupling efficiency during a recharge session. For example, based on screen 128, a clinician may identify that the highest recharge coupling efficiency of the four posture states was detected while patient 12 occupied a reclining posture state, and the lowest recharge coupling efficiency of the four posture states was detected while patient 12 occupied a lying posture state. Based on this information, a clinician may instruct patient 12 to attempt to occupy a reclining posture state during future recharge sessions if possible while avoiding a lying posture state. In this manner, such information may be used to help tailor the posture state behavior of patient 12 during future recharge sessions to provide for a relatively efficient, and therefore, relatively fast recharge of power source 90 of IMD 14.

FIG. 10 is a flow diagram illustrating another example technique that may be employed while recharging example rechargeable power source 90 of an IMD. For ease of illustration, the example of FIG. 10 is described as being performed by processor 80 of IMD 14, in other examples, processor 104 of programmer 20 and/or a processor of another device may perform all or a part of the example technique shown in FIG. 10. Also, for ease of illustration, the technique of FIG. 10 was described with regard to processor 104 receiving and monitoring posture sensor data in the form of the output signals generated for each axis of a three-axis accelerometer, although other types of posture sensor data are contemplated.

As shown in FIG. 10, throughout a recharge session, processor 80 may receive sampled values from the output signal of each axis of posture sensor 89 (132). Processor 80 may analyze the signal values received during the recharge session to detect any changes in the output of one or more axes greater than a threshold amount (134). In some examples, the threshold amount may be defined to correspond to movement of patient 12 and/or IMD 14 beyond some nominal amount. For example, the threshold amount may be defined to detect changes in the output of posture sensor 89 that generally correspond to posture changes of patient 12, and/or bumps or other mechanical forces applied to IMD 14. In some examples, the threshold amount may be defined based on activity counts. In some examples, the threshold amount may be defined based on the sample-to-sample signal difference that is significantly greater than the sample-to-sample signal differences we see while patient 12 is mobile. For example, the sample-to-sample signal differences while mobile could be characterized during the design of IMD 14 or some other time before IMD 14 is implanted, or may be determined in real-time during a learning period after IMD 14 is implanted. Based on the sampled data, a "bump" threshold may be set with some margin above the largest mobile differential.

Processor 80 may determine the amount of change in the signal output for each axis on a signal-by-signal basis in which the change is approximately equal to the difference between the most recently sampled value and second most recently sampled value. Processor 80 may additionally or alternatively detect changes in the output of posture sensor signal based on rolling averages for the sampled values. A similar process may be employed in which an M of N approach is used. For example, if M is equal to 4 and N is equal to 6, then if 4 of 6 values measured in a row are greater than the threshold value, then processor 80 may determine a disturbance that triggers a determination of the recharge coupling efficiency.

If processor 80 detects that any changes in the value of the output for one or more axes that is greater than the threshold amount, processor 80 may detect the recharge coupling efficiency at or near the time of the detected change in response (136). For example, processor 80 may determine the current in and/or voltage in secondary coil 91 and/or primary coil 113 of programmer 20 at approximately the same time the change in the output of posture sensor 89 was detected. In some examples, processor 80 may additionally make such measurements for some nominal period of time before and/or after the detected change in the output of posture sensor 89.

Based on the values of current and/or voltage determined in response to the detect change in posture sensor output, processor 80 may determine the recharge coupling efficiency (136), and associate the recharge coupling efficiency with the disturbance detected in the output signal of posture sensor 89 (138). Processor 80 may store information associating one or more details of the signal disturbance (e.g., overall change in signal values) and the recharge coupling efficiency determine in response to the detection of the disturbance in memory 82 (FIG. 3). In some examples, processor 80 may transmit the associated information to programmer 20, e.g., to inform a user of the recharge coupling efficiency detected in response to the detected disturbance, during the recharge session or at some later point.

Processor 80 may continue to monitor the output of posture sensor 89 for disturbances until the recharge session is complete (140). In this manner, processor 80 may detect the occurrence of multiple different signal disturbances throughout a recharge session, and associate each occurrence with recharge coupling efficiency, as described. In some examples, the end of a recharge session may be detected by processor 80 by the lack of current in secondary coil 91 for some predefined period of time, or communicated to processor 80 by programmer 20.

The information resulting from the example of FIG. 10 may be reviewed by a clinician or other user, e.g., via user interface 106 of programmer 20. In some examples, such information may be used as a diagnostic tool when troubleshooting issue with the process used to recharge the power source of an IMD. For example, as noted above, such information could help a patient understand which postures are better for recharging. Moreover, it might show that posture changes (such as to walking) or other actions characterized by a threshold disturbance in the posture sensor signal may significantly degrade recharge coupling efficiency and, thus, should be avoided.

In another example, patient 12 may complain about issues with recharge (such as, e.g., recharge taking a relatively long time). If a clinician reviews the gathered information, which reflects a degradation of recharge coupling due to numerous disturbances in the sensor signal, then the clinician would simply attempt to train patient 12 to better sit still during a recharges session. In order to use the diagnostic this way, IMD 14 may need to record the signal disturbance along with the previous recharge coupling efficiency value, and then the updated recharge coupling efficiency value after taking another measurement.

In some examples, including those of FIGS. 7, 8, and 10, the information collected by system 10 may allow the user or processor to relate patient posture state with recharge efficiencies during one or more recharge sessions. Such information may allow a user or processor to identify one or more posture states of patient 12 that provide for desirable recharge coupling efficiency and/or identify one or more posture states of patient 12 that provide for undesirable recharge coupling efficiency on a patient specific basis.

As noted above, for ease of illustration, the example technique of FIG. 10 was described with regard processor 104 receiving and monitoring posture sensor data in the form of the output signal values sampled from each axis of a three-axis accelerometer to identify variations in posture sensor data. However, examples using other types of posture sensor data are contemplated. For example, rather than analyzing respective signal output of each axis of a three-axis accelerometer on an individual basis, processor 80 may analyze the posture sensor data on the basis of the magnitude of the coordinate vector derived from the sampled values for each axis. In such examples, processor 80 may monitor such a magnitude to detect the occurrence of changes in the magnitude greater than a threshold value, and associate the recharge coupling efficiency determined in response to the disturbance as described above. Additionally or alternatively, processor 80 may monitor the posture state data to detect one or more changes in the posture state occupied by patient 12, and associate the recharge coupling efficiency determined in response to the detection of the posture state change in a similar fashion.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a computer-readable medium. Computer-readable media may include non-transitory computer storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples of the disclosure have been described. Various modifications may be made without departing from the scope of the claims. These and other examples are within the scope of the following claims.

The invention claimed is:

1. A method comprising:
   determining recharge coupling efficiency for an implantable medical device during a recharge session;
   receiving posture sensor data generated by a posture sensor during the recharge session; and
   associating the recharge coupling efficiency determined during the recharge session with the posture sensor data,
   wherein at least one of the determining, receiving, and associating is performed via at least one processor.

2. The method of claim 1, further comprising determining one or more posture states of a patient during the recharge session based on the posture sensor data,
   wherein determining recharge coupling efficiency for an implantable medical device during a recharge session comprises determining recharge coupling efficiency during each of the one or more posture states of the patient, and
   wherein associating the recharge coupling efficiency determined during the recharge session with the posture sensor data comprises associating the recharge coupling efficiency determined for each of the one or more posture states with the respective posture states.

3. The method of claim 2, further comprising determining a total time occupied for each of the one or more posture states determined during the recharge session.

4. The method of claim 3, further comprising displaying, via a user interface of an external device, an indicator indicating at least one of the total time occupied for each of the one or more posture states and the recharge coupling efficiency during each of the one or more posture states.

5. The method of claim 1, further comprising detecting one or more variations in the received posture sensor data during the recharge session based on a comparison to a threshold value,
   wherein determining recharge coupling efficiency for an implantable medical device during a recharge session comprises determining recharge coupling efficiency for the implantable medical device during the recharge session based at least on the detection of the one or more variations in the received posture sensor data.

6. The method of claim 1, wherein the posture sensor comprises a multiple-axis accelerometer sensor, wherein the posture sensor data includes at least one of signal output values for respective axes or a magnitude vector determined based on signal output values from respective axes generated by the posture sensor.

7. The method of claim 1, further comprising:
determining a posture state of the patient based on the posture sensor data; and
delivering therapy to the patient via the implantable medical device based on the determined posture state of the patient.

8. The method of claim 7, wherein the therapy comprises electrical stimulation therapy.

9. The method of claim 1, wherein the recharge session comprises a first recharge session, and the posture sensor data comprises first posture sensor data, the method further comprising:
determining recharge coupling efficiency for the implantable medical device during a second recharge session;
receiving second posture sensor data generated by the posture sensor during the second recharge session;
associating the recharge coupling efficiency determined during the second recharge session with the second posture sensor data; and
combining the recharge coupling efficiency and second posture sensor data from the second recharge session with the recharge coupling efficiency and first posture sensor data from the first recharge session.

10. The method of claim 1, wherein associating the recharge coupling efficiency determined during the recharge session with the posture sensor data comprises associating, on a temporal basis, the recharge coupling efficiency determined during the recharge session with the posture sensor data.

11. The method of claim 10, further comprising determining a posture state occupied by the patient at a time during the recharge session based on the posture sensor data,
wherein determining recharge coupling efficiency for the implantable medical device during a recharge session comprises determining recharge coupling efficiency for the implantable medical device at the time during the recharge session, and
wherein associating, on the temporal basis, the recharge coupling efficiency determined during the recharge session with the posture sensor data comprises associating the recharge coupling efficiency determined at the time during the recharge session with the patient state occupied by the patient at the time during the recharge session.

12. A system comprising:
a rechargeable power source of an implantable medical device;
a recharge module configured to recharge the rechargeable power source via inductive energy transfer;
a posture sensor configured to generate posture sensor data; and
at least one processor configured to determine recharge coupling efficiency during a recharge session, receive posture sensor data generated by the posture sensor during the recharge session, and associate the recharge coupling efficiency determined during the recharge session with the posture sensor data.

13. The system of claim 12, wherein at least one processor is configured to determine one or more posture states of a patient during the recharge session based on the posture sensor data,
wherein at least one processor determines recharge coupling efficiency for an implantable medical device during a recharge session by at least determining recharge coupling efficiency during each of the one or more posture states of the patient, and
wherein at least one processor associates the recharge coupling efficiency determined during the recharge session with the posture sensor data by at least associating the recharge coupling efficiency determined for each of the one or more posture states with the respective posture states.

14. The system of claim 13, wherein at least one processor is configured to determine a total time occupied for each of the one or more posture states determined during the recharge session.

15. The system of claim 14, further comprising a user interface of an external device, wherein at least one processor is configured to generate an indicator indicating at least one of the total time occupied for each of the one or more posture states and the recharge coupling efficiency during each of the one or more posture states, and display the indicator via the user interface.

16. The system of claim 12, wherein at least one processor is configured to detect one or more variations in the received posture sensor data during the recharge session based on a comparison to a threshold value,
wherein at least one processor determines the recharge coupling efficiency for an implantable medical device during a recharge session by at least determining recharge coupling efficiency for the implantable medical device during the recharge session based at least on the detection of the one or more variations in the received posture sensor data.

17. The system of claim 12, wherein the posture sensor comprises a multiple-axis accelerometer sensor, wherein the posture sensor data includes at least one of signal output values for respective axes or a magnitude vector determined based on signal output values from respective axes generated by the posture sensor.

18. The system of claim 12, wherein at least one processor is configured to determine a posture state of the patient based on the posture sensor data, and control delivery of therapy to the patient by the implantable medical device based on the determined posture state of the patient.

19. The system of claim 18, wherein the therapy comprises electrical stimulation therapy.

20. The system of claim 12,
wherein the recharge session comprises a first recharge session, and the posture sensor data comprises first posture sensor data,
wherein at least one processor is configured to determine recharge coupling efficiency for the implantable medical device during a second recharge session, receive second posture sensor data generated by the posture sensor during the second recharge session, associate the recharge coupling efficiency determined during the second recharge session with the second posture sensor data, and combine the recharge coupling efficiency and second posture sensor data from the second recharge session with the recharge coupling efficiency and first posture sensor data from the first recharge session.

21. The system of claim 12, wherein the at least one processor is configured to associate, on a temporal basis, the recharge coupling efficiency determined during the recharge session with the posture sensor data.

22. The system of claim 21, wherein the at least one processor is configured to determine a posture state occupied by the patient at a time during the recharge session based on the posture sensor data, determine the recharge coupling efficiency for the implantable medical device at the time during the recharge session, and associate the recharge coupling efficiency determined at the time during the recharge session with the patient state occupied by the patient at the time during the recharge session.

23. A system comprising:
   means for determining recharge coupling efficiency for an implantable medical device during a recharge session;
   means for receiving posture sensor data generated by a posture sensor during the recharge session; and
   means for associating the recharge coupling efficiency determined during the recharge session with the posture sensor data.

24. A non-transitory computer-readable storage medium comprising instructions to cause one or more processors to:
   determine recharge coupling efficiency for an implantable medical device during a recharge session;
   receive posture sensor data generated by a posture sensor during the recharge session; and
   associate the recharge coupling efficiency determined during the recharge session with the posture sensor data.

* * * * *